(12) United States Patent
McCarthy

(10) Patent No.: US 9,751,835 B2
(45) Date of Patent: Sep. 5, 2017

(54) PROCESSES AND INTERMEDIATES FOR PREPARING INDOLE PHARMACEUTICALS

(71) Applicant: INDIANA UNIVERSITY RESEARCH AND TECHNOLOGY CORPORATION, Indianapolis, IN (US)

(72) Inventor: James R. McCarthy, Indianapolis, IN (US)

(73) Assignee: Indiana University Research and Technology Corporation, Indianapolis, IN (US)

( * ) Notice: Subject to any disclaimer, the term of this patent is extended or adjusted under 35 U.S.C. 154(b) by 0 days.

(21) Appl. No.: 14/890,514

(22) PCT Filed: May 13, 2014

(86) PCT No.: PCT/US2014/037783
§ 371 (c)(1),
(2) Date: Nov. 11, 2015

(87) PCT Pub. No.: WO2014/186325
PCT Pub. Date: Nov. 20, 2014

(65) Prior Publication Data
US 2016/0107991 A1    Apr. 21, 2016

Related U.S. Application Data

(60) Provisional application No. 61/823,668, filed on May 15, 2013.

(51) Int. Cl.
| | | |
|---|---|---|
| C07D 209/04 | (2006.01) | |
| C07D 401/12 | (2006.01) | |
| C07D 403/12 | (2006.01) | |
| C07D 209/14 | (2006.01) | |
| B01J 23/44 | (2006.01) | |
| C07C 249/16 | (2006.01) | |
| C07D 295/135 | (2006.01) | |

(52) U.S. Cl.
CPC ........... *C07D 209/14* (2013.01); *B01J 23/44* (2013.01); *C07C 249/16* (2013.01); *C07D 295/135* (2013.01); *C07D 403/12* (2013.01)

(58) Field of Classification Search
CPC ... C07D 209/04; C07D 401/12; C07D 403/12
USPC ................... 540/602; 546/205; 548/465, 509
See application file for complete search history.

(56) References Cited

U.S. PATENT DOCUMENTS

| | | |
|---|---|---|
| 5,998,402 A | 12/1999 | Miller et al. |
| 7,683,051 B2 | 3/2010 | Demerson et al. |
| 7,683,052 B2 | 3/2010 | Ali et al. |
| 8,034,807 B2 | 10/2011 | Jiman et al. |
| 2010/0016290 A1 | 1/2010 | Cotarca et al. |
| 2010/0016581 A1 | 1/2010 | Andreella et al. |
| 2010/0016582 A1 | 1/2010 | Soriato et al. |

FOREIGN PATENT DOCUMENTS

| | | |
|---|---|---|
| EP | 1777214 | 4/2007 |
| WO | 99/19293 | 4/1999 |
| WO | 00/51982 | 9/2000 |
| WO | 2011/022596 | 2/2011 |
| WO | 2012/007453 | 1/2012 |

OTHER PUBLICATIONS

PCT International Search Report and Written Opinion completed by the ISA/EP on Jul. 15, 2014 and issued in connection with PCT/US2014/037783.
Samsoniya, S., et al. "1,7-Migration of Benzyl Group in 2-Substituted N-Benzylindoles" Chemistry of Heterocyclic Compounds, vol. 33, No. 5, 1997, pp. 527-531, XP002727169.
Samsoniya, S., et al. "Unexpected Migration of the Benzyl Group in N-Benzylindoles" Chemistry of Heterocyclic Compounds, vol. 30, No. 8, 1994, pp. 993-994, XP00272170.
Bellamy, A., et al. "EZ-Isomerism in Alkyl Phenyl Ketone Phenylhydrazones and Acetaldehyde Phenylhydrazone" Journal of the Chemical Society. Perkin Transactions 1: Organic and Bioorganic Chemistry., Jan. 1, 1976, pp. 456-458. XP00272171.
Dettmann, et al. "2-Phenyl-1-[4-(2-piperidine-1-yl-ethoxy)benzyl]-1H-benzimidazoles as Ligands for the Estrogen Receptor: Synthesis and Pharmacological Evaluation" Bioorganic & Medicinal Chemistry. Pergamon. GB., vol. 18, No. 14. Jul. 15, 2010, pp. 4905-4916, XP027263451.
Miller, et al., "Design, Synthesis, and Preclinical Characterization of Novel, Highly Selective Indole Estrogens", J. Med. Chem. 2001, 44, 1654-1657.
Yadav, et al., "Design, synthesis and bioevaluation of novel candidate selective estrogen receptor modulators", European J. Med. Chem. 2011, 46, 3858-3866.
Bravo-Altamirant, et al., "Synthesis and Structure-Activity Relationships of Benzothienothiazepinone Inhibitors of Protein Kinase D", ACS Med. Chem. Lett., 2:154-159 (2011).

*Primary Examiner* — Brenda Coleman
(74) *Attorney, Agent, or Firm* — Barnes & Thornburg LLP

(57) ABSTRACT

The invention described herein pertains to processes and intermediates for preparing indole containing pharmaceuticals, particularly to processes and intermediates for preparing selective estrogen receptor modulators, such as bazedoxifene.

22 Claims, No Drawings

PROCESSES AND INTERMEDIATES FOR PREPARING INDOLE PHARMACEUTICALS

CROSS REFERENCE TO RELATED APPLICATION

This application is a U.S. national stage application under 35 U.S.C. §371(b) of international application serial No. PCT/US2014/037783 filed May 13, 2014, which claims the benefit under 35 U.S.C. §119(e) of U.S. provisional patent application No. 61/823,668, filed May 15, 2013, the entirety of the disclosures of which are expressly incorporated herein by reference.

TECHNICAL FIELD

The invention described herein pertains to processes and intermediates for preparing indole containing pharmaceuticals. In particular, the described herein pertains to processes and intermediates for preparing selective estrogen receptor modulators, such as bazedoxifene.

BACKGROUND AND SUMMARY OF THE INVENTION

Given the importance of indole drugs, efficient, cost-effective, and high purity yielding synthetic and manufacturing processes are needed.

For example, bazedoxifene and pipendoxifene each belongs to the class of selective oestrogen receptor modulators (SERMs). SERMs are defined as substances that bind to the oestrogen (also known as estrogen) receptor with high affinity and at the same time have do not show significant binding activity with other nuclear receptors. In contrast to oestrogens, however, they lead in the various target tissues to "oestrogen-agonistic" or "oestrogen-antagonistic" action. Bazedoxifene is effective in the prevention and treatment of osteoporosis and in particular of postmenopausal osteoporosis.

Several synthetic processes have been reported for bazedoxifene (see, for example, U.S. Pat. Nos. 5,998,402, 7,683,051, 7,683,052, and 8,034,807, US application publication Nos. 2010/0016290, 2010/0016581, and 2010/0016582, EP published application No. 1777214, and PCT international application publication Nos. WO 99/019293, WO 2011/022596, and WO 2012/007453). However, current and conventional processes have been reported to be expensive due to a number of factors, including the cost of reagents, the necessary isolation and purification of intermediates by chromatography, and yield losses due to unwanted side reactions, including C-alkylation during formation of the N-1 substituted indoles.

It has been discovered that the processes described herein for preparing indole drugs, such as but not limited to bazedoxifene, pipendoxifene, and the like, provide the desired compound with high efficiency, low cost, and with fewer accompanying side products than conventional processes. In addition, it has been discovered that the processes described herein for preparing indole drugs, such as but not limited to bazedoxifene, pipendoxifene, and the like, provide several crystalline intermediates that improve overall purity and in high yield.

In one illustrative embodiment of the invention, processes for preparing compounds of the following formula are described herein:

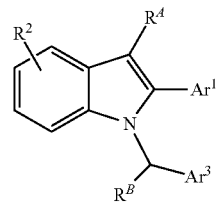

and pharmaceutically acceptable salts thereof, wherein $Ar^1$, $Ar^2$, and $Ar^3$ are each independently selected aryl, each of which is optionally substituted;

$R^A$ is hydrogen, or optionally substituted alkyl or optionally substituted arylalkyl;

$R^B$ is hydrogen, or optionally substituted alkyl or optionally substituted arylalkyl; and $R^2$ is hydrogen, or represents one or more aryl substituents, including but not limited to hydroxy and derivatives thereof.

In another illustrative embodiment, the processes described herein include one or more of the following steps:

(a) contacting a first compound of the formula

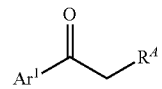

with a second compound of the formula $Ar^2$—NHNH$_2$ or a salt thereof; and/or (b) contacting a first compound of the formula

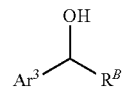

or a salt thereof, with a reagent capable of converting the hydroxyl group into a leaving group to form a second compound of the formula

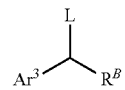

or a salt thereof, where L is the leaving group; and/or (c) contacting a first compound of the formula

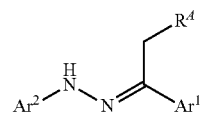

with a second compound of the formula

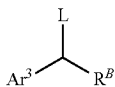

or a salt thereof, and a base; and/or (d) contacting a compound of the formula

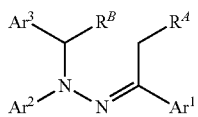

with an acid.

In another illustrative embodiment, the processes described herein are used to prepare compounds of the foregoing formulae, where one or more of $Ar^1$, $Ar^2$, and/or $Ar^3$ is an independently selected protected phenol. In another embodiment, the processes described herein include the step of (e) contacting the protected phenol with a phenol deprotecting agent. In another embodiment, the processes described herein include the step of (f) crystallizing the deprotected phenol in the presence of an acid, or a carboxylic acid, or acetic acid to form the corresponding acid addition salt thereof.

In another embodiment, intermediate compounds useful for preparing the compounds of the foregoing formulae are described herein, including compounds of the formulae

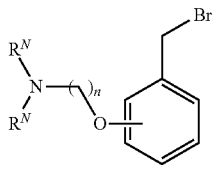

and salts thereof, such as the HBr salt thereof; where n is 2, 3, 4, or 5; and each $R^N$ is independently selected from hydrogen and alkyl, heteroalkyl, arylalkyl, and heteroarylalkyl, each of which is optionally substituted, or both $R^N$ and the attached nitrogen are taken together to form a heterocyclyl radical.

In another embodiment, intermediate compounds useful for preparing the compounds of the foregoing formulae are described herein, including compounds of the formulae

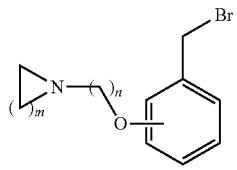

and salts thereof, such as the HBr salt thereof; wherein n is 2, 3, 4, or 5; and m is 1, 2, 3, 4, 5, 6, or 7; and various subgenera and species thereof.

In another embodiment, intermediate compounds useful for preparing the compounds of the foregoing formulae are described herein, including compounds of the formulae

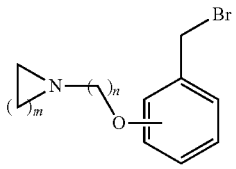

and salts thereof, such as the HBr salt thereof; wherein n is 2, 3, 4, or 5; and m is 1, 2, 3, 5, 6, or 7; and various subgenera and species thereof.

It is appreciated herein that the foregoing benzyl bromide intermediates may be advantageously isolated and used in the processes descried herein as the corresponding salts, such as the HBr salts, instead of the neutral amino compounds.

In another embodiment, intermediate compounds useful for preparing the compounds of the foregoing formulae are described herein, including compounds of the formulae

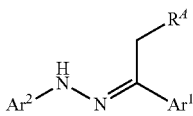

and salts thereof, wherein $Ar^1$ and $Ar^2$ are each independently selected aryl, each of which is optionally substituted; and $R^A$ is hydrogen, or optionally substituted alkyl or optionally substituted arylalkyl; and various subgenera and species thereof.

In another embodiment, intermediate compounds useful for preparing the compounds of the foregoing formulae are described herein, including compounds of the formulae

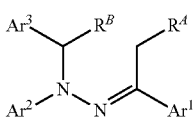

and salts thereof, wherein $Ar^1$, $Ar^2$, and $Ar^3$ are each independently selected aryl, each of which is optionally substituted; $R^A$ is hydrogen, or optionally substituted alkyl or optionally substituted arylalkyl; and $R^B$ is hydrogen, or optionally substituted alkyl or optionally substituted arylalkyl; and various subgenera and species thereof.

In another embodiment, pharmaceutical compositions containing one or more of the compounds are also described herein. In one aspect, the compositions include a therapeutically effective amount of the one or more compounds for treating a patient with a disease responsive to a selective estrogen receptor modulator (SERM). It is to be understood that the compositions may include other component and/or ingredients, including, but not limited to, other therapeutically active compounds, and/or one or more carriers, diluents, excipients, and the like. In another embodiment, the compounds and pharmaceutical compositions for treating patients with a disease responsive to a SERM are also described herein as being included in methods for using or treating, uses, and uses in the manufacture of medicaments.

DETAILED DESCRIPTION

Several illustrative embodiments of the invention are described by the following enumerated clauses:

1. A process for preparing a compound of the formula

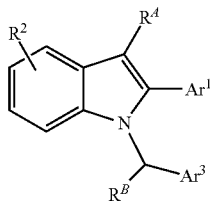

or a pharmaceutically acceptable salt thereof, wherein
$Ar^1$, $Ar^2$, and $Ar^3$ are each independently selected aryl, each of which is optionally substituted;
$R^A$ is hydrogen, or optionally substituted alkyl or optionally substituted arylalkyl;
$R^B$ is hydrogen, or optionally substituted alkyl or optionally substituted arylalkyl; and
$R^2$ is hydrogen, or represents one or more an aryl substituents, such as but not limited to hydroxy and derivatives thereof; the process comprising the step of:

(a) contacting a first compound of the formula

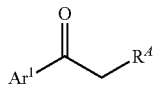

with a second compound of the formula

or a salt thereof; or (b) contacting a first compound of the formula

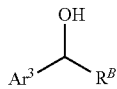

or a salt thereof, with a reagent capable of converting the hydroxyl group into a leaving group to form a second compound of the formula

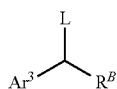

or a salt thereof, where L is the leaving group; or (c) contacting a first compound of the formula

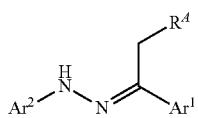

with a second compound of the formula

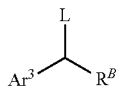

or a salt thereof, and a base; or (d) contacting a compound of the formula

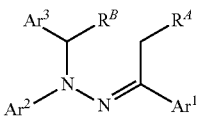

with an acid; or
any combination of any of the foregoing steps.

1A. The process of clause 1 wherein
$Ar^1$ is phenyl bearing a group $R^3$ at the 2- or 3-position and a group $R^4$ at the 4-position;
$Ar^2$ is phenyl bearing a group $R^{2B}$ at the 2- or 3-position and a group $R^{2A}$ at the 4-position;
$Ar^3$ is phenyl bearing a groups $R^5$ and $R^6$ at the 2-, 3-, 5- or 3-positions and a group —O—$(CH_2)$—Y at the 4-position;
$R^A$ is selected from H, $C_1$-$C_6$ alkyl, cyano, nitro, trifluoromethyl, and halogen;
$R^B$ is hydrogen;
$R^2$ denotes a group $R^{2A}$ at the 5-position of the indole and a further group $R^{2B}$ on the benzene ring of the indole wherein $R^{2A}$ is selected from H, OH, —O—C(O)—$C_1$-$C_{12}$ alkyl (straight chain or branched), —O—$C_1$-$C_{12}$ alkyl (straight chain or branched or cyclic), or halogens; or $C_1$-$C_4$ halogenated ethers;
$R^1$ is selected from H, OH, —O—C(O)—$C_1$-$C_{12}$ alkyl (straight chain or branched), —O—$C_1$-$C_{12}$ alkyl (straight chain or branched or cyclic), or halogens; or $C_1$-$C_4$ halogenated ethers;
$R^{2B}$, $R^3$, $R^4$, $R^5$, and $R^6$ are independently selected from H, OH, —O—C(O)—$C_1$-$C_{12}$ alkyl (straight chain or branched), —O—$C_1$-$C_{12}$ alkyl (straight chain or branched or cyclic), halogens, or $C_1$-$C_4$ halogenated ethers, cyano, $C_1$-$C_6$ alkyl (straight chain or branched), or trifluoromethyl, with the proviso that, when $R^{2A}$ is H, $R^{2B}$ is not OH;
n is 2 or 3;
Y is the moiety

wherein:
a) $R^7$ and $R^8$ are independently selected from the group of H, $C_1$-$C_6$ alkyl, or phenyl optionally substituted by CN, $C_1$-$C_6$ alkyl (straight chain or branched), $C_1$-$C_6$ alkoxy (straight chain or branched), halogen, —OH, —$CF_3$, or —$OCF_3$; or
b) $R_7$ and $R_8$ are concatenated to form a five-membered saturated heterocycle containing one nitrogen heteroatom, the heterocycle being optionally substituted with 1-3 substituents independently selected from the group consisting of hydrogen, hydroxyl, halo, $C_1$-$C_4$ alkyl, trihalomethyl, $C_1$-$C_4$ alkoxy, trihalomethoxy, $C_1$-$C_4$ acyloxy, $C_1$-$C_4$ alkylthio, $C_1$-$C_4$ alkylsulfinyl, $C_1$-$C_4$ alkylsulfonyl, hydroxy($C_1$-$C_4$)

alkyl, —CO₂H, —CN—, —CONHR¹, —NH₂, —NH(C₁-C₄ alkyl), —N(C₁-C₄ alkyl)₂, —NHSO₂R¹, —NHCOR¹, —NO₂, or phenyl optionally substituted with 1-3 (C₁-C₄) alkyl; or c) R⁷ and R⁸ are concatenated to form a six-membered saturated heterocycle containing one nitrogen heteroatom, the heterocycle being optionally substituted with 1-3 substituents independently selected from the group consisting of hydrogen, hydroxyl, halo, C₁-C₄ alkyl, trihalomethyl, C₁-C₄ alkoxy, trihalomethoxy, C₁-C₄ acyloxy, C₁-C₄ alkylthio, C₁-C₄ alkylsulfinyl, C₁-C₄ alkylsulfonyl, hydroxy(C₁-C₄) alkyl, —CO₂H, —CN, —CONHR₁, —NH₂, —NH(C₁-C₄ alkyl), —N(C₁-C₄ alkyl)₂, —NHSO₂R¹, —NHCOR¹, —NO₂, or phenyl optionally substituted with 1-3 (C₁-C₄) alkyl; or d) R⁷ and R⁸ are concatenated to form a seven-membered saturated heterocycle containing one nitrogen heteroatom, the heterocycle being optionally substituted with 1-3 substituents independently selected from the group consisting of hydrogen, hydroxyl, halo, C₁-C₄ alkyl, trihalomethyl, C₁-C₄ alkoxy, trihalomethoxy, C₁-C₄ acyloxy, C₁-C₄ alkylthio, C₁-C₄ alkylsulfinyl, C₁-C₄ alkylsulfonyl, hydroxy(C₁-C₄) alkyl, —CO₂H, —CN, —CONHR₁, —NH₂, —NH(C₁-C₄ alkyl), —N(C₁-C₄ alkyl)₂, —NHSO₂R¹, —NHCOR¹, —NO₂, or phenyl optionally substituted with 1-3 (C₁-C₄) alkyl; or e) R⁷ and R⁸ are concatenated to form an eight-membered saturated heterocycle containing one nitrogen heteroatom, the heterocycle being optionally substituted with 1-3 substituents independently selected from the group consisting of hydrogen, hydroxyl, halo, C₁-C₄ alkyl, trihalomethyl, C₁-C₄ alkoxy, trihalomethoxy, C₁-C₄ acyloxy, C₁-C₄ alkylthio, C₁-C₄ alkylsulfinyl, C₁-C₄ alkylsulfonyl, hydrox(C₁-C₄) alkyl, —CO₂H, —CN, —CONHR¹, —NH₂, —NH(C₁-C₄ alkyl), —N(C₁-C₄ alkyl)₂, —NHSO₂R¹, —NHCOR¹, —NO₂, or phenyl optionally substituted with 1-3 (C₁-C₄) alkyl; or f) R⁷ and R⁸ are concatenated to form a saturated bicyclic heterocycle containing from 6-12 carbon atoms either bridged or fused and containing one nitrogen heteroatom, the heterocycle being optionally substituted with 1-3 substituents independently selected from the group consisting of hydrogen, hydroxyl, halo, C₁-C₄ alkyl, trihalomethyl, C₁-C₄ alkoxy, trihalomethoxy, C₁-C₄ acyloxy, C₁-C₄ alkylthio, C₁-C₄ alkylsulfinyl, C₁-C₄ alkylsulfonyl, hydroxy(C₁-C₄) alkyl, —CO₂H, —CN, —CONHR¹, —NH₂, —NH(C₁-C₄ alkyl), —N(C₁-C₄ alkyl)₂, —NHSO₂R¹, —NHCOR¹, —NO₂, or phenyl optionally substituted with 1-3 (C₁-C₄) alkyl;

or a pharmaceutically acceptable salt thereof.

1B. The process of clause 1A wherein

R¹ and R²ᴬ are independently selected from H, OH, —O—C(O)—C₁-C₄ alkyl, or —O—C₁-C₄ alkyl, or halogen;

R²ᴮ, R³, R⁴, R⁵, and R⁶ are independently selected from H, OH, —O—C(O)—C₁-C₄ alkyl, —O—C₁-C₄ alkyl, halogen, or trifluoromethyl, with the proviso that, when R²ᴬ is H, R²ᴮ is not OH;

R⁴ is selected from H, C₁-C₆ alkyl, cyano, nitro, trifluoromethyl, and halogen;

Y is the moiety

wherein:

R⁷ and R⁸ are selected independently from H, C₁-C₆ alkyl, or combined by —(CH₂)ₚ—, wherein p is an integer of from 2 to 6, so as to form a saturated ring, the ring being optionally substituted by up to three substituents selected from the group of hydrogen, hydroxyl, halo, C₁-C₄ alkyl, trihalomethyl, C₁-C₄ alkoxy, trihalomethoxy, C₁-C₄ alkylthio, C₁-C₄ alkylsulfinyl, C₁-C₄ alkylsulfonyl, hydrox(C₁-C₄) alkyl, —CO₂H, —CN, —CONH(C₁-C₄) alkyl, —NH₂, —NH(C₁-C₄ alkyl), —N(C₁-C₄ alkyl)₂, —NHSO₂(C₁-C₄) alkyl, —NHCO(C₁-C₄) alkyl, or —NO₂;

or a pharmaceutically acceptable salt thereof.

2. The process of the preceding clause 1, 1A or 1B wherein the contacting step (a) is performed at a pH of less than about 7.

3. The process of any one of the preceding clauses wherein the second compound in step (a) is a salt, or the HCl salt; and the contacting step (a) is performed in the presence of less than about 1 equivalent of a base.

4. The process of any one of the preceding clauses wherein the base is an inorganic base, such as NaHCO₃.

5. The process of any one of the preceding clauses wherein the reagent capable of converting the hydroxyl group into a leaving group is a halogenating agent, such as PBr₃

6. The process of any one of the preceding clauses wherein the base in step (c) is a hydride base, such as NaH.

7. The process of any one of the preceding clauses wherein the acid in step (d) is a carboxylic acid, such as AcOH.

8. A compound of the formula

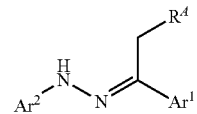

or a salt thereof, wherein

Ar¹ and Ar² are each independently selected aryl, each of which is optionally substituted; and Rᴬ is hydrogen, or optionally substituted alkyl or optionally substituted arylalkyl.

9. A compound of the formula

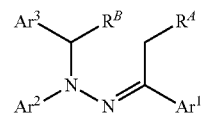

or a salt thereof, wherein

Ar¹, Ar², and Ar³ are each independently selected aryl, each of which is optionally substituted;

Rᴬ is hydrogen, or optionally substituted alkyl or optionally substituted arylalkyl; and Rᴮ is hydrogen, or optionally substituted alkyl or optionally substituted arylalkyl.

10. The process or compound of any one of the preceding clauses wherein each of Ar¹ and Ar² is a phenyl substituted with an electron donating group.

11. The process or compound of any one of the preceding clauses wherein each of Ar¹, Ar², and Ar³ is a protected phenol, where each protected phenol is independently selected.

12. The process or compound of any one of the preceding clauses wherein each of $Ar^1$ and $Ar^2$ is an independently selected protected phenol.

13. The process or compound of any one of the preceding clauses wherein each protected phenol is an independently selected optionally substituted benzyl protected phenol.

14. The process or compound of any one of the preceding clauses wherein each protected phenol is a benzyl protected phenol.

15. The process or compound of any one of the preceding clauses wherein $Ar^1$ and $Ar^2$ are 4-benzyloxyphenyl.

16. The process of any one of the preceding clauses further comprising the step of (e) contacting the protected phenol with a phenol deprotecting agent.

17. The process of clause 16 wherein the phenol deprotecting agent is a debenzylating agent.

18. The process of clause 16 wherein the phenol deprotecting agent is a reducing agent.

19. The process of clause 18 wherein the reducing agent is hydrogen gas in the presence of a metal catalyst.

20. The process of clause 18 wherein the reducing agent is ammonium formate in the presence of a metal catalyst.

21. The process of clause 19 or 20 wherein the metal catalyst is palladium, such as palladium on carbon.

22. The process of any one of the preceding clauses wherein the protected phenol is a compound of the formula

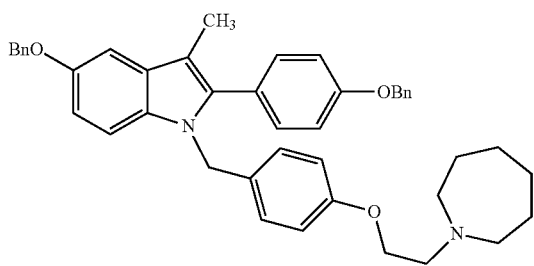 [SMILES: Cc1c(-c2ccc(OCc3ccccc3)cc2)n(Cc2ccc(OCCN3CCCCCC3)cc2)c2ccc(OCc3ccccc3)cc12]

or a pharmaceutically acceptable salt thereof.

23. The process of any one of the preceding clauses wherein the protected phenol is a compound of the formula

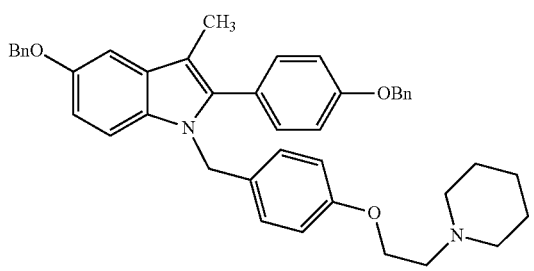 [SMILES: Cc1c(-c2ccc(OCc3ccccc3)cc2)n(Cc2ccc(OCCN3CCCCC3)cc2)c2ccc(OCc3ccccc3)cc12]

or a pharmaceutically acceptable salt thereof.

24. The process of any one of the preceding clauses further comprising the step of (f) crystallizing the deprotected phenol in the presence of an acid, or a carboxylic acid, or acetic acid to form the corresponding acid addition salt thereof.

25. The process or compound of any one of the preceding clauses wherein $Ar^1$ is halobenzyloxyphenyl, or 4-chlorobenzyloxyphenyl.

26. The process or compound of any one of the preceding clauses wherein $Ar^1$ is 4-benzyloxyphenyl.

27. The process or compound of any one of the preceding clauses wherein $Ar^1$ is 4-hydroxyphenyl.

28. The process or compound of any one of the preceding clauses wherein $R^2$ is hydroxy or a derivative thereof.

29. The process or compound of any one of the preceding clauses wherein $R^2$ is hydroxy or protected hydroxy.

30. The process or compound of any one of the preceding clauses wherein $R^2$ is benzyloxy, or 5-benzyloxy.

31. The process or compound of any one of the preceding clauses wherein $R^2$ is hydroxy, or 5-hydroxy.

32. The process or compound of any one of the preceding clauses wherein $R^4$ is optionally substituted alkyl.

33. The process or compound of any one of the preceding clauses wherein $R^4$ is alkyl, or methyl.

34A. The process or compound of any one of the preceding clauses wherein $R^B$ is optionally substituted alkyl.

34B. The process or compound of any one of the preceding clauses wherein $R^B$ is alkyl, or methyl.

35. The process or compound of any one of the preceding clauses wherein $R^B$ is hydrogen.

36. The process or compound of any one of the preceding clauses wherein L is bromo.

37. The process or compound of any one of the preceding clauses wherein $Ar^3$ is a radical of the formula

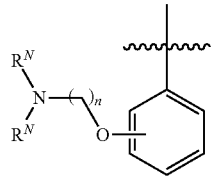

where n is 2, 3, 4, or 5; and each $R^N$ is independently selected from hydrogen and alkyl, heteroalkyl, arylalkyl, and heteroarylalkyl, each of which is optionally substituted, or both $R^N$ and the attached nitrogen are taken together to form a heterocyclyl radical.

38. The process or compound of any one of the preceding clauses wherein n is 2.

39. The process or compound of any one of the preceding clauses wherein the heterocyclyl radical is aziridinyl, pyrolidinyl, piperidinyl, or homopiperidinyl, each of which is optionally substituted.

40. The process or compound of any one of the preceding clauses wherein the heterocyclyl radical is homopiperidinyl.

41. The process or compound of any one of the preceding clauses wherein $Ar^3$ is a radical of the formula

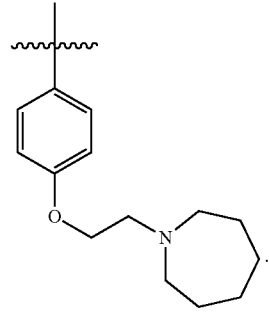

42. The process or compound of any one of the preceding clauses wherein $Ar^3$ is a radical of the formula

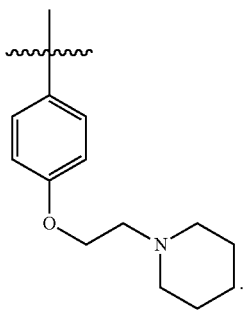

43. The process or compound of any one of the preceding clauses wherein the compound of the formula

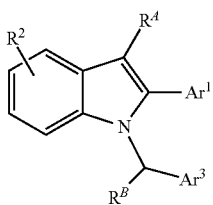

is a compound of the formula

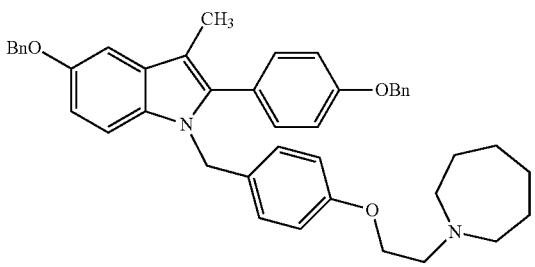 [SMILES: Cc1c(-c2ccc(OCc3ccccc3)cc2)n(Cc2ccc(OCCN3CCCCCC3)cc2)c2ccc(OCc3ccccc3)cc12]

or a pharmaceutically acceptable salt thereof.

44. The process or compound of any one of the preceding clauses wherein the compound of the formula

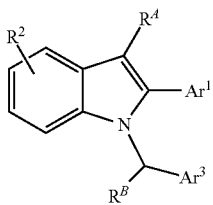

is a compound of the formula

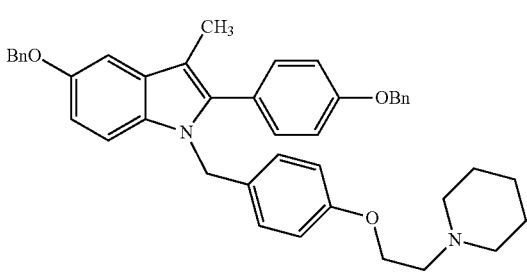 [SMILES: Cc1c(-c2ccc(OCc3ccccc3)cc2)n(Cc2ccc(OCCN3CCCCC3)cc2)c2ccc(OCc3ccccc3)cc12]

or a pharmaceutically acceptable salt thereof.

45. The process of any one of the preceding clauses wherein the compound of the formula

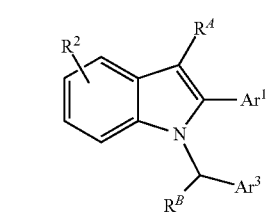

is bazedoxifene, or a pharmaceutically acceptable salt thereof, or the acetic acid salt thereof.

46. The process of any one of the preceding clauses wherein the compound of the formula

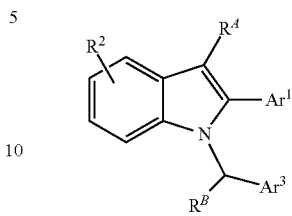

is pipendoxifene, or a pharmaceutically acceptable salt thereof, or the acetic acid salt thereof.

47. The process of any one of the preceding clauses wherein the first compound of step (c) is of the formula

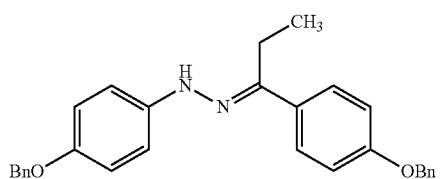 [SMILES: CC/C(=N\Nc1ccc(OCc2ccccc2)cc1)c1ccc(OCc2ccccc2)cc1]

or a salt thereof.

48. The process of any one of the preceding clauses wherein the second compound of step (c) is of the formula

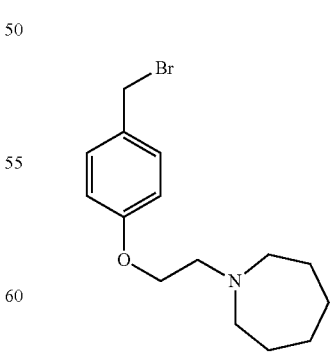

or a salt thereof, or the HBr salt thereof.

49. The process of any one of the preceding clauses wherein the second compound of step (c) is of the formula

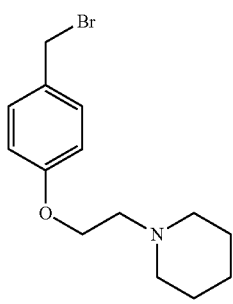 [SMILES: BrCc1ccc(OCCN2CCCCC2)cc1]

or a salt thereof, or the HBr salt thereof.

50. The process of any one of the preceding clauses wherein the compound of step (d) is of the formula

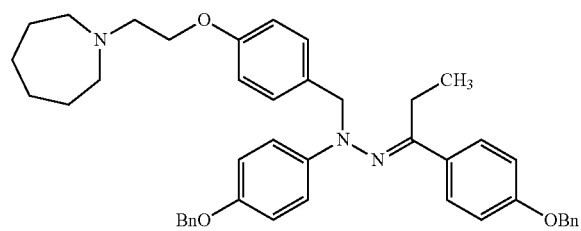 [SMILES: CC/C(=N\N(Cc1ccc(OCCN2CCCCCC2)cc1)c1ccc(OCc2ccccc2)cc1)c1ccc(OCc2ccccc2)cc1]

or a salt thereof.

51. The process of any one of the preceding clauses wherein the compound of step (d) is of the formula

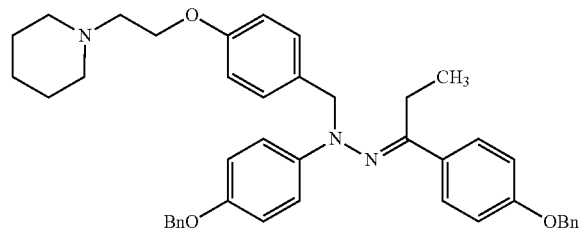 [SMILES: CC/C(=N\N(Cc1ccc(OCCN2CCCCC2)cc1)c1ccc(OCc2ccccc2)cc1)c1ccc(OCc2ccccc2)cc1]

or a salt thereof.

52. A compound of the formula

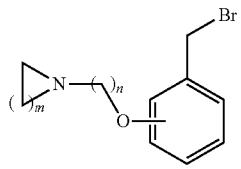

or a salt thereof, or the HBr salt thereof; wherein n is 2, 3, 4, or 5; and m is 1, 2, 3, 5, 6, or 7.

53. The compound of clause 52 wherein the compound is of the formula

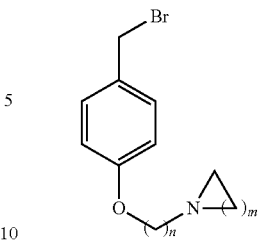

or a salt thereof, or the HBr salt thereof.

54. The compound of any one of clauses 52 to 53 wherein n is 2.

55. The compound of any one of clauses 52 to 54 wherein m is 5.

56. The compound of any one of clauses 52 to 54 wherein m is 6.

In reciting the foregoing collection of clauses, it is to be understood that all possible combinations of features, and all possible subgenera and sub-combinations are described. For example, it is to be understood that when each of $Ar^1$ and $Ar^2$ is a phenyl substituted with an electron donating group, $R^B$ may be optionally substituted alkyl, or alternatively, alkyl, or alternatively, methyl, and so forth. Similarly, when $Ar^3$ is a radical of the formula

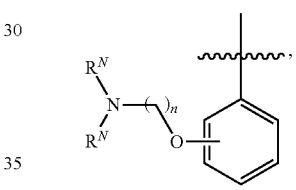

$Ar^1$ may be halobenzyloxyphenyl, or alternatively 4-chlorobenzyloxyphenyl, or alternatively, 4-hydroxyphenyl, and so forth. Similarly, when $Ar^1$ is 4-benzyloxyphenyl, $R^2$ may be hydroxy or a derivative thereof, and $R^B$ may be alkyl, or methyl, and so forth. Other combinations, subgenera, and sub-combinations are also described by the collection of clauses.

In each of the foregoing and each of the following embodiments, it is to be understood that the formulae include and represent not only all pharmaceutically acceptable salts of the compounds, but also include any and all hydrates and/or solvates of the compound formulae. It is appreciated that certain functional groups, such as the hydroxy, amino, and like groups form complexes and/or coordination compounds with water and/or various solvents, in the various physical forms of the compounds. Accordingly, the above formulae are to be understood to include and represent those various hydrates and/or solvates.

In each of the foregoing and each of the following embodiments, it is also to be understood that the formulae include and represent each possible isomer, such as stereoisomers and geometric isomers, both individually and in any and all possible mixtures. In each of the foregoing and each of the following embodiments, it is also to be understood that the formulae include and represent any and all crystalline forms, partially crystalline forms, and non crystalline and/or amorphous forms of the compounds.

The compounds described herein may contain one or more chiral centers, or may otherwise be capable of existing as multiple stereoisomers. It is to be understood that in one embodiment, the invention described herein is not limited to any particular sterochemical requirement, and that the compounds, and compositions, methods, uses, and medicaments that include them may be optically pure, or may be any of a variety of stereoisomeric mixtures, including racemic and other mixtures of enantiomers, other mixtures of diastereomers, and the like. It is also to be understood that such mixtures of stereoisomers may include a single stereochemical configuration at one or more chiral centers, while including mixtures of stereochemical configuration at one or more other chiral centers.

Similarly, the compounds described herein may include geometric centers, such as cis, trans, E, and Z double bonds. It is to be understood that in another embodiment, the invention described herein is not limited to any particular geometric isomer requirement, and that the compounds, and compositions, methods, uses, and medicaments that include them may be pure, or may be any of a variety of geometric isomer mixtures. It is also to be understood that such mixtures of geometric isomers may include a single configuration at one or more double bonds, while including mixtures of geometry at one or more other double bonds.

As used herein, the term "alkyl" includes a chain of carbon atoms, which is optionally branched. As used herein, the terms "alkenyl" and "alkynyl" each include a chain of carbon atoms, which is optionally branched, and include at least one double bond or triple bond, respectively. It is to be understood that alkynyl may also include one or more double bonds. It is to be further understood that in certain embodiments, alkyl is advantageously of limited length, including $C_1$-$C_{24}$, $C_1$-$C_{12}$, $C_1$-$C_8$, $C_1$-$C_6$, and $C_1$-$C_4$. Illustratively, such particularly limited length alkyl groups, including $C_1$-$C_8$, $C_1$-$C_6$, and $C_1$-$C_4$ may be referred to as lower alkyl. It is to be further understood that in certain embodiments alkenyl and/or alkynyl may each be advantageously of limited length, including $C_2$-$C_{24}$, $C_2$-$C_{12}$, $C_2$-$C_8$, $C_2$-$C_6$, and $C_2$-$C_4$. Illustratively, such particularly limited length alkenyl and/or alkynyl groups, including $C_2$-$C_8$, $C_2$-$C_6$, and $C_2$-$C_4$ may be referred to as lower alkenyl and/or alkynyl. It is appreciated herein that shorter alkyl, alkenyl, and/or alkynyl groups may add less lipophilicity to the compound and accordingly will have different pharmacokinetic behavior. In embodiments of the invention described herein, it is to be understood, in each case, that the recitation of alkyl refers to alkyl as defined herein, and optionally lower alkyl. In embodiments of the invention described herein, it is to be understood, in each case, that the recitation of alkenyl refers to alkenyl as defined herein, and optionally lower alkenyl. In embodiments of the invention described herein, it is to be understood, in each case, that the recitation of alkynyl refers to alkynyl as defined herein, and optionally lower alkynyl. Illustrative alkyl, alkenyl, and alkynyl groups are, but not limited to, methyl, ethyl, n-propyl, isopropyl, n-butyl, isobutyl, sec-butyl, tert-butyl, pentyl, 2-pentyl, 3-pentyl, neopentyl, hexyl, heptyl, octyl, and the like, and the corresponding groups containing one or more double and/or triple bonds, or a combination thereof.

As used herein, the term "alkylene" includes a divalent chain of carbon atoms, which is optionally branched. As used herein, the term "alkenylene" and "alkynylene" includes a divalent chain of carbon atoms, which is optionally branched, and includes at least one double bond or triple bond, respectively. It is to be understood that alkynylene may also include one or more double bonds. It is to be further understood that in certain embodiments, alkylene is advantageously of limited length, including $C_1$-$C_{24}$, $C_1$-$C_{12}$, $C_1$-$C_8$, $C_1$-$C_6$, and $C_1$-$C_4$. Illustratively, such particularly limited length alkylene groups, including $C_1$-$C_8$, $C_1$-$C_6$, and $C_1$-$C_4$ may be referred to as lower alkylene. It is to be further understood that in certain embodiments alkenylene and/or alkynylene may each be advantageously of limited length, including $C_2$-$C_{24}$, $C_2$-$C_{12}$, $C_2$-$C_8$, $C_2$-$C_6$, and $C_2$-$C_4$. Illustratively, such particularly limited length alkenylene and/or alkynylene groups, including $C_2$-$C_8$, $C_2$-$C_6$, and $C_2$-$C_4$ may be referred to as lower alkenylene and/or alkynylene. It is appreciated herein that shorter alkylene, alkenylene, and/or alkynylene groups may add less lipophilicity to the compound and accordingly will have different pharmacokinetic behavior. In embodiments of the invention described herein, it is to be understood, in each case, that the recitation of alkylene, alkenylene, and alkynylene refers to alkylene, alkenylene, and alkynylene as defined herein, and optionally lower alkylene, alkenylene, and alkynylene. Illustrative alkyl groups are, but not limited to, methylene, ethylene, n-propylene, isopropylene, n-butylene, isobutylene, sec-butylene, pentylene, 1,2-pentylene, 1,3-pentylene, hexylene, heptylene, octylene, and the like.

As used herein, the term "cycloalkyl" includes a chain of carbon atoms, which is optionally branched, where at least a portion of the chain in cyclic. It is to be understood that cycloalkylalkyl is a subset of cycloalkyl. It is to be understood that cycloalkyl may be polycyclic. Illustrative cycloalkyl include, but are not limited to, cyclopropyl, cyclopentyl, cyclohexyl, 2-methylcyclopropyl, cyclopenteth-2-yl, adamantyl, and the like. As used herein, the term "cycloalkenyl" includes a chain of carbon atoms, which is optionally branched, and includes at least one double bond, where at least a portion of the chain in cyclic. It is to be understood that the one or more double bonds may be in the cyclic portion of cycloalkenyl and/or the non-cyclic portion of cycloalkenyl. It is to be understood that cycloalkenylalkyl and cycloalkylalkenyl are each subsets of cycloalkenyl. It is to be understood that cycloalkyl may be polycyclic. Illustrative cycloalkenyl include, but are not limited to, cyclopentenyl, cyclohexylethen-2-yl, cycloheptenylpropenyl, and the like. It is to be further understood that chain forming cycloalkyl and/or cycloalkenyl is advantageously of limited length, including $C_3$-$C_{24}$, $C_3$-$C_{12}$, $C_3$-$C_8$, $C_3$-$C_6$, and $C_5$-$C_6$. It is appreciated herein that shorter alkyl and/or alkenyl chains forming cycloalkyl and/or cycloalkenyl, respectively, may add less lipophilicity to the compound and accordingly will have different pharmacokinetic behavior.

As used herein, the term "heteroalkyl" includes a chain of atoms that includes both carbon and at least one heteroatom, and is optionally branched. Illustrative heteroatoms include nitrogen, oxygen, and sulfur. In certain variations, illustrative heteroatoms also include phosphorus, and selenium. As used herein, the term "cycloheteroalkyl" including heterocyclyl and heterocycle, includes a chain of atoms that includes both carbon and at least one heteroatom, such as heteroalkyl, and is optionally branched, where at least a portion of the chain is cyclic. Illustrative heteroatoms include nitrogen, oxygen, and sulfur. In certain variations, illustrative heteroatoms also include phosphorus, and selenium. Illustrative cycloheteroalkyl include, but are not limited to, tetrahydrofuryl, pyrrolidinyl, tetrahydropyranyl, piperidinyl, morpholinyl, piperazinyl, homopiperazinyl, quinuclidinyl, and the like.

As used herein, the term "aryl" includes monocyclic and polycyclic aromatic carbocyclic groups, each of which may be optionally substituted. Illustrative aromatic carbocyclic groups described herein include, but are not limited to, phenyl, naphthyl, and the like. As used herein, the term "heteroaryl" includes aromatic heterocyclic groups, each of which may be optionally substituted. Illustrative aromatic heterocyclic groups include, but are not limited to, pyridinyl, pyrimidinyl, pyrazinyl, triazinyl, tetrazinyl, quinolinyl, quinazolinyl, quinoxalinyl, thienyl, pyrazolyl, imidazolyl, oxazolyl, thiazolyl, isoxazolyl, isothiazolyl, oxadiazolyl, thiadiazolyl, triazolyl, benzimidazolyl, benzoxazolyl, benzthiazolyl, benzisoxazolyl, benzisothiazolyl, and the like.

As used herein, the term "amino" includes the group $NH_2$, alkylamino, and dialkylamino, where the two alkyl groups in dialkylamino may be the same or different, i.e. alkylalkylamino. Illustratively, amino includes methylamino, ethylamino, dimethylamino, methylethylamino, and the like. In addition, it is to be understood that when amino modifies or is modified by another term, such as aminoalkyl, or acylamino, the above variations of the term amino are included therein. Illustratively, aminoalkyl includes $H_2N$-alkyl, methylaminoalkyl, ethylaminoalkyl, dimethylaminoalkyl, methylethylaminoalkyl, and the like. Illustratively, acylamino includes acylmethylamino, acylethylamino, and the like.

As used herein, the term "amino and derivatives thereof" includes amino as described herein, and alkylamino, alkenylamino, alkynylamino, heteroalkylamino, heteroalkenylamino, heteroalkynylamino, cycloalkylamino, cycloalkenylamino, cycloheteroalkylamino, cycloheteroalkenylamino, arylamino, arylalkylamino, arylalkenylamino, arylalkynylamino, heteroarylamino, heteroarylalkylamino, heteroarylalkenylamino, heteroarylalkynylamino, acylamino, and the like, each of which is optionally substituted. The term "amino derivative" also includes urea, carbamate, and the like.

As used herein, the term "hydroxy and derivatives thereof" includes OH, and alkyloxy, alkenyloxy, alkynyloxy, heteroalkyloxy, heteroalkenyloxy, heteroalkynyloxy, cycloalkyloxy, cycloalkenyloxy, cycloheteroalkyloxy, cycloheteroalkenyloxy, aryloxy, arylalkyloxy, arylalkenyloxy, arylalkynyloxy, heteroaryloxy, heteroarylalkyloxy, heteroarylalkenyloxy, heteroarylalkynyloxy, acyloxy, and the like, each of which is optionally substituted. The term "hydroxy derivative" also includes carbamate, and the like.

As used herein, the term "thio and derivatives thereof" includes SH, and alkylthio, alkenylthio, alkynylthio, heteroalkylthio, heteroalkenylthio, heteroalkynylthio, cycloalkylthio, cycloalkenylthio, cycloheteroalkylthio, cycloheteroalkenylthio, arylthio, arylalkylthio, arylalkenylthio, arylalkynylthio, heteroarylthio, heteroarylalkylthio, heteroarylalkenylthio, heteroarylalkynylthio, acylthio, and the like, each of which is optionally substituted. The term "thio derivative" also includes thiocarbamate, and the like.

As used herein, the term "acyl" includes formyl, and alkylcarbonyl, alkenylcarbonyl, alkynylcarbonyl, heteroalkylcarbonyl, heteroalkenylcarbonyl, heteroalkynylcarbonyl, cycloalkylcarbonyl, cycloalkenylcarbonyl, cycloheteroalkylcarbonyl, cycloheteroalkenylcarbonyl, arylcarbonyl, arylalkylcarbonyl, arylalkenylcarbonyl, arylalkynylcarbonyl, heteroarylcarbonyl, heteroarylalkylcarbonyl, heteroarylalkenylcarbonyl, heteroarylalkynylcarbonyl, acylcarbonyl, and the like, each of which is optionally substituted.

As used herein, the term "carboxylic acid and derivatives thereof" includes the group $CO_2H$ and salts thereof, and esters and amides thereof, and CN.

As used herein, the term "sulfonic acid or a derivative thereof" includes $SO_3H$ and salts thereof, and esters and amides thereof.

As used herein, the term "sulfonyl" includes alkylsulfonyl, alkenylsulfonyl, alkynylsulfonyl, heteroalkylsulfonyl, heteroalkenylsulfonyl, heteroalkynylsulfonyl, cycloalkylsulfonyl, cycloalkenylsulfonyl, cycloheteroalkylsulfonyl, cycloheteroalkenylsulfonyl, arylsulfonyl, arylalkylsulfonyl, arylalkenylsulfonyl, arylalkynylsulfonyl, heteroarylsulfonyl, heteroarylalkylsulfonyl, heteroarylalkenylsulfonyl, heteroarylalkynylsulfonyl, acylsulfonyl, and the like, each of which is optionally substituted.

The term "optionally substituted" as used herein includes the replacement of hydrogen atoms with other functional groups on the radical that is optionally substituted. Such other functional groups illustratively include, but are not limited to, amino, hydroxyl, halo, thiol, alkyl, haloalkyl, heteroalkyl, aryl, arylalkyl, arylheteroalkyl, heteroaryl, heteroarylalkyl, heteroarylheteroalkyl, nitro, sulfonic acids and derivatives thereof, carboxylic acids and derivatives thereof, and the like. Illustratively, any of amino, hydroxyl, thiol, alkyl, haloalkyl, heteroalkyl, aryl, arylalkyl, arylheteroalkyl, heteroaryl, heteroarylalkyl, heteroarylheteroalkyl, and/or sulfonic acid is optionally substituted.

As used herein, the terms "optionally substituted aryl" and "optionally substituted heteroaryl" include the replacement of hydrogen atoms with other functional groups on the aryl or heteroaryl that is optionally substituted. Such other functional groups illustratively include, but are not limited to, amino, hydroxy, halo, thio, alkyl, haloalkyl, heteroalkyl, aryl, arylalkyl, arylheteroalkyl, heteroaryl, heteroarylalkyl, heteroarylheteroalkyl, nitro, sulfonic acids and derivatives thereof, carboxylic acids and derivatives thereof, and the like. Illustratively, any of amino, hydroxy, thio, alkyl, haloalkyl, heteroalkyl, aryl, arylalkyl, arylheteroalkyl, heteroaryl, heteroarylalkyl, heteroarylheteroalkyl, and/or sulfonic acid is optionally substituted.

Illustrative substituents include, but are not limited to, a radical $—(CH_2)_xZ^X$, where x is an integer from 0-6 and $Z^X$ is selected from halogen, hydroxy, alkanoyloxy, including $C_1$-$C_6$ alkanoyloxy, optionally substituted aroyloxy, alkyl, including $C_1$-$C_6$ alkyl, alkoxy, including $C_1$-$C_6$ alkoxy, cycloalkyl, including $C_3$-$C_8$ cycloalkyl, cycloalkoxy, including $C_3$-$C_8$ cycloalkoxy, alkenyl, including $C_2$-$C_6$ alkenyl, alkynyl, including $C_2$-$C_6$ alkynyl, haloalkyl, including $C_1$-$C_6$ haloalkyl, haloalkoxy, including $C_1$-$C_6$ haloalkoxy, halocycloalkyl, including $C_3$-$C_8$ halocycloalkyl, halocycloalkoxy, including $C_3$-$C_8$ halocycloalkoxy, amino, $C_1$-$C_6$ alkylamino, $(C_1$-$C_6$ alkyl)($C_1$-$C_6$ alkyl)amino, alkylcarbonylamino, $N$—$(C_1$-$C_6$ alkyl)alkylcarbonylamino, aminoalkyl, $C_1$-$C_6$ alkylaminoalkyl, $(C_1$-$C_6$ alkyl)($C_1$-$C_6$ alkyl)aminoalkyl, alkylcarbonylaminoalkyl, $N$—$(C_1$-$C_6$ alkyl)alkylcarbonylaminoalkyl, cyano, and nitro; or $Z^X$ is selected from $—CO_2R^4$ and $—CONR^5R^6$, where $R^4$, $R^5$, and $R^6$ are each independently selected in each occurrence from hydrogen, $C_1$-$C_6$ alkyl, aryl-$C_1$-$C_6$ alkyl, and heteroaryl-$C_1$-$C_6$ alkyl.

As used herein, the terms "treating", "contacting" or "reacting" when referring to a chemical reaction generally mean to add or mix two or more reagents under appropriate conditions that allows a chemical transformation or chemical reaction to take place, and/or to produce the indicated and/or the desired product. It is to be understood that the reaction which produces the indicated and/or the desired product may not necessarily result directly from the combination of two reagents which were initially added. In other words, there may be one or more intermediates which are produced in the mixture which ultimately leads to the formation of the indicated and/or the desired product.

As used herein, the term "composition" generally refers to any product comprising the specified ingredients in the specified amounts, as well as any product which results, directly or indirectly, from combinations of the specified ingredients in the specified amounts. It is to be understood that the compositions described herein may be prepared from isolated compounds described herein or from salts, solutions, hydrates, solvates, and other forms of the compounds described herein. It is also to be understood that the compositions may be prepared from various amorphous, non-amorphous, partially crystalline, crystalline, and/or other morphological forms of the compounds described herein. It is also to be understood that the compositions may be prepared from various hydrates and/or solvates of the compounds described herein. Accordingly, such pharmaceutical compositions that recite compounds described herein are to be understood to include each of, or any combination of, the various morphological forms and/or solvate or hydrate forms of the compounds described herein. Illustratively, compositions may include one or more carriers, diluents, and/or excipients. The compounds described herein, or compositions containing them, may be formulated in a therapeutically effective amount in any conventional dosage forms appropriate for the methods described herein. The compounds described herein, or compositions containing them, including such formulations, may be administered by a wide variety of conventional routes for the methods described herein, and in a wide variety of dosage formats, utilizing known procedures (see generally, Remington: The Science and Practice of Pharmacy, (21$^{st}$ ed., 2005)).

The term "therapeutically effective amount" as used herein, refers to that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated. In one aspect, the therapeutically effective amount is that which may treat or alleviate the disease or symptoms of the disease at a reasonable benefit/risk ratio applicable to any medical treatment. However, it is to be understood that the total daily usage of the compounds and compositions described herein may be decided by the attending physician within the scope of sound medical judgment. The specific therapeutically-effective dose level for any particular patient will depend upon a variety of factors, including the disorder being treated and the severity of the disorder; activity of the specific compound employed; the specific composition employed; the age, body weight, general health, gender and diet of the patient: the time of administration, route of administration, and rate of excretion of the specific compound employed; the duration of the treatment; drugs used in combination or coincidentally with the specific compound employed; and like factors well known to the researcher, veterinarian, medical doctor or other clinician of ordinary skill.

In another embodiment, the compounds described herein are prepared according to the following illustrative process

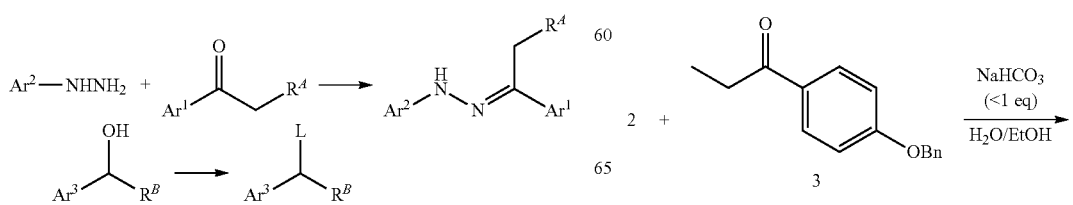

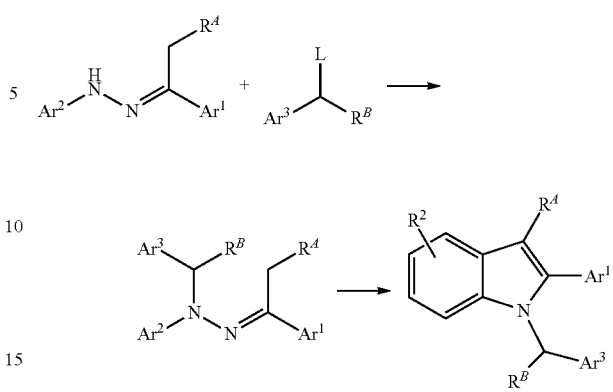

In another embodiment, the compounds described herein are prepared according to the following illustrative process

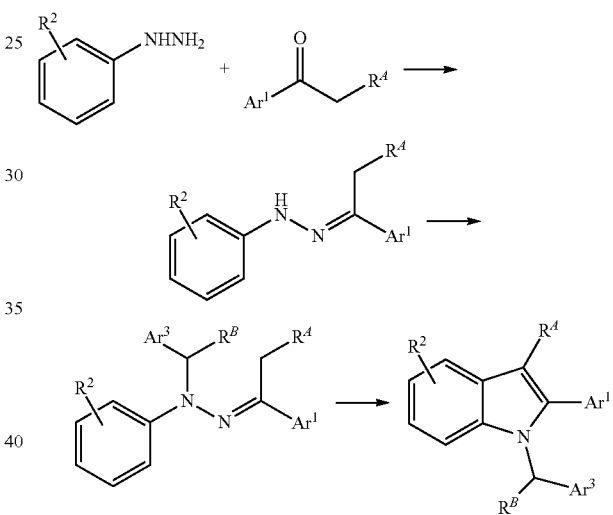

In another embodiment, the compounds described herein are prepared according to the following illustrative process

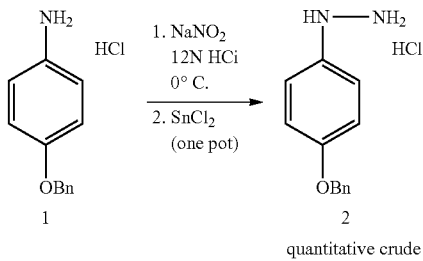

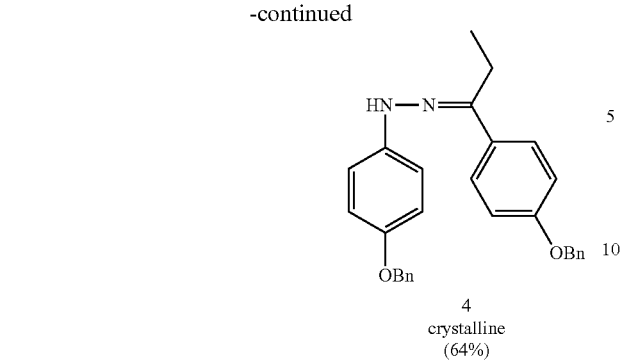
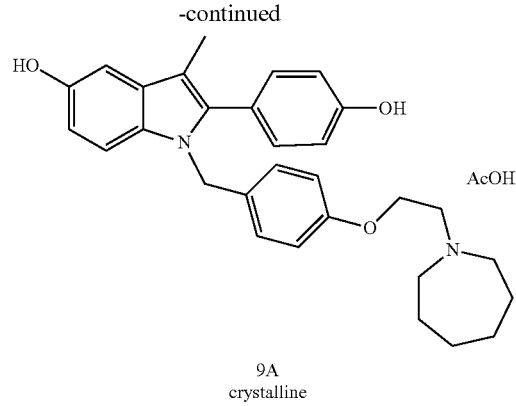
In another embodiment, the compounds described herein are prepared according to the following illustrative process
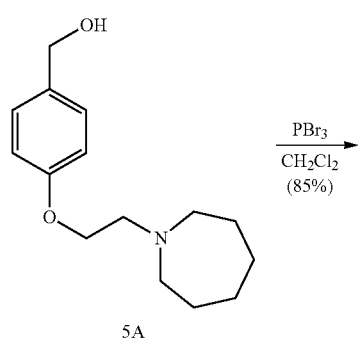
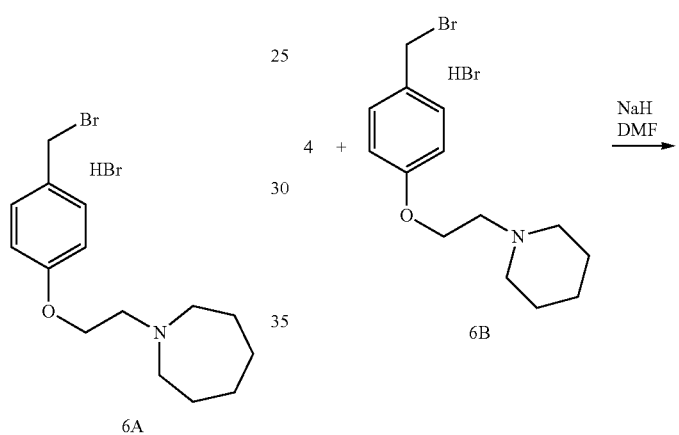
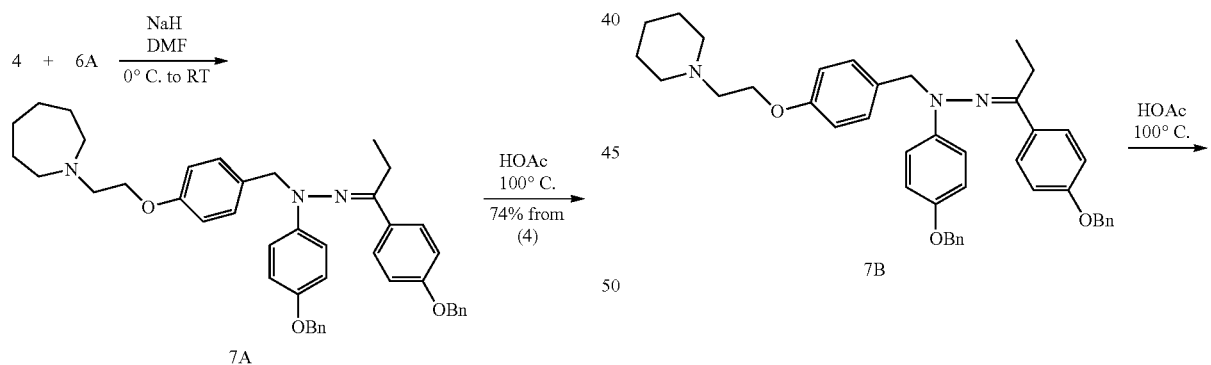
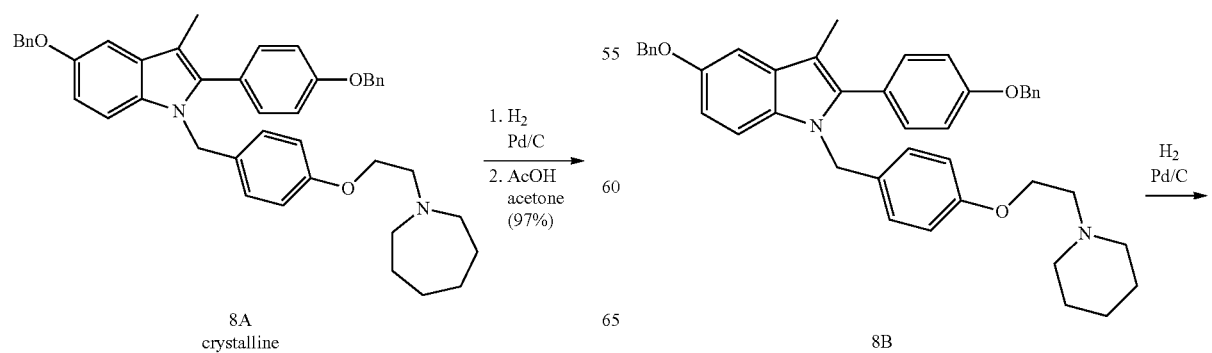

-continued

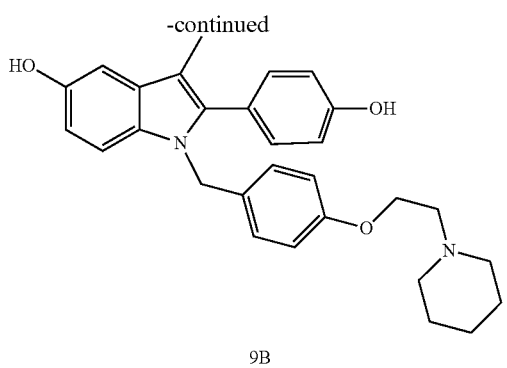

9B

Compound 6B is disclosed by Dettman et al., in Biorg. Med. Chem., 18:4905-16 (2010), the disclosure of which is incorporated herein by reference. Compound 6B may be prepared as described herein from the corresponding benzylalcohol. Optionally, compound 9B may be isolated as a pharmaceutically acceptable salt, as described herein.

The following examples further illustrate specific embodiments of the invention; however, the following illustrative examples should not be interpreted in any way to limit the invention.

EXAMPLES

Example

Products are analyzed by LCMS (dissolving the product in acetonitrile) under the following conditions: Column: Agilent Eclipse XDB-C18, 5 uM, 4.6×150 mm, Solvent A: 5 mM Ammonium acetate in Water, Solvent B: 5 mM Ammonium acetate in $CH_3CN$:MeOH (1:1), Time 0 min: 20% B, Time 10 min: 100% B, Duration of run: 15 min, Gradient elution flow rate: 1.00 ml/min.

Example 1-(4-Benzyloxy)phenyl-2-(1-(4-(benzyloxy)phenyl)-propylidenehydrazine (4). 4-(Benzyloxy)phenylhydrazine hydrochloride (2) is obtained as described by Bravo-Altamirant et al., in ACS Med. Chem. Lett., 2:154-159 (2011), the disclosure of which is incorporated herein by reference. Compound 2 (7.9 g, 31.6 mmol) (finely ground), 4-benzyloxypropiophenone (3) (6 g, 25 mmol) and ethanol (200 mL) are added to a 1 L round bottom flask with football stirring bar and reflux condenser with an argon inlet valve on top. A solution of $NaHCO_3$ (1.9 g, 22.5 mmol) in water (35 mL) is added and the reaction mixture is heated to reflux (oil bath) with stirring under argon. A homogenous light brown solution forms, which slowly turns orange, becoming cloudy, and a white solid crystalizes from the reaction mixture. The progress of the reaction is monitored by LCMS and after 1 hr. If essentially all of the hydrazine 2 (retention time 8.1 min) has condensed with the ketone 3 (retention time 10.9 min) forming desired hydrazone 4 (retention time 12.25 min) and unreacted 3 remains, an additional 2.5 g (10 mmol) of 2 in ethanol (20 mL) (as a mixture) and 380 mg (4.5 mmol) of sodium bicarbonate dissolved in water (5 ml) are added to the reaction. After an additional 2 hrs at reflux LCMS shows only desired hydrazone product. The reaction mixture is cooled in an ice bath to ambient temperature and the mass of white crystals are collected by filtration and washed with cold ethanol and hexane. The crystals are optionally dissolved in refluxing toluene (50 mL), followed by gravity filtration, and recrystallized from toluene/hexane (50 ml). The solution is cooled in an ice bath with stirring yielding white crystals. The crystal slurry of 4 is stored at −15° C. for 2 h, and 4 is collected by filtration and washed with hexane (7 g, 64%). LCMS Retention time 12.25 min (96%) m/e 437. Compound 4 darkens on storage unless placed under argon at −15° C.

Example 1-(2-(4-Bromomethyl)phenoxy)ethyl)azepane hydrobromide (6A). (4-(2-(Azepan-1-yl)ethyl)phenyl)methanol hydrochloride (5A) is obtained as described by Yadav et al., in European J. Med. Chem. 2011, 46, 3858-3866. Compound 5A (8.7 g, 30 mmol) and methylene chloride (60 mL) are added to a 250 mL round bottom flask with drying tube and the mixture is cooled in an ice bath with stirring. A solution of $PBr_3$ (6 mL, 60 mmol) in methylene chloride (15 mL) is slowly added to the cold reaction with stirring. The resulting clear colorless solution is stirred in the ice bath for 3 h and stored at −15° C. over night. The colorless reaction mixture is poured into a stirring solution of hexane (300 ml). The resulting white crystalline precipitate is stirred for 1 h at ambient temperature, and the crystals are collected by filtration and washed with hexane. The crystals are optionally recrystallized from acetonitrile (110 ml) and cooling in an ice bath with stirring and stored over night at −15° C. The crystals of 6 are collected by filtration and dried in a vacuum oven at ambient temperature (10 g, 85%). The crystals are optionally recrystallized from acetone. NMR (DMSO-d6) δ 9.55 (br s, 1H), 7.42 (d, 2H, J=8.7 Hz), 6.99 (d, 2H, J=8.7 Hz), 4.71 (s, 2H), 4.36 (t, 2H, J=5.1 Hz), 3.57 (br q, 2H), 3.45 (m, 2H), 3.25 (m, 2H), 1.83 (m, 4H), 1.61 (m, 4H).

Example 1-(2-(4-((1-(4-Benzyloxy)phenyl)-2-(1-(4-(benzyloxy) phenyl)-propylidene)hydrazinyl)methyl)phenoxy)ethyl)azepan (7A). To a dry 1 L 3-neck round bottom flask with football stirring bar, argon inlet valve and rubber septum is added 60% NaH oil dispersion (4.6 g, 120 mmol). The NaH is washed with hexane (100 mL) to remove the oil, decanting the hexane from the flask. Dry THF (40 mL) and dry DMF (120 mL) are canulated into the flask and the reaction flask is cooled in an ice bath. 1-(4-Benzyloxy)phenyl)-2-(1-4-(benzyloxy)phenyl)propylidene(hydrazine (4) (6.6 g, 14.7 mmol) is added to the reaction mixture with stirring. The reaction mixture turns orange with anion formation, and gas evolution is observed. The reaction is stirred for 15 min in the ice bath under argon and 1-(4-bromomethyl)phenethyl) azepane hydrobromide (6A) (7.1 g, 18 mmol) is then added. The ice bath was removed and the reaction is allowed to warm to ambient temperature. The reaction progress is monitored by TLC (EtOAc:Hexane 1:2, then $CH_2Cl_2$:MeOH 9:1). Reaction allowed to continue an additional 3 hrs. The reaction progress is also monitored by LCMS for major peak formation at retention time 13.4 min (m/e 668). The reaction is poured into ice water (250 ml) and extracted with EtOAc (3×75 mL). The combined organic layers are washed with brine (4×75 mL), dried (MgSO$_4$) and evaporated to a dark yellow oil to 7A (12.4 g versus 9.75 g calculated). LCMS Retention time 13.4 min (83.5%) m/e 668. The material is sufficiently pure to carry on directly in the next step.

Example 1-(4-(2-(Azepan-1-yl)ethoxy)benzyl)-5-(benzyloxy)-2-(4-benzyloxy)phenyl)-3-methyl-1H-indole (8A). 1-(2-(4-((1-(4-Benzyloxy)phenyl)-2-(1-(4-(benzyloxy)phenyl)propylidene)hydrazinyl)methyl)phenoxy)ethyl)azepan (7A) (12.4 g,) and glacial acetic acid (150 mL) are added to a 500 ml round bottom flask with stirring bar and placed under an argon atmosphere. The yellow solution is heated at 100° C. (oil bath) and the progress of the reaction is monitored by TLC and LCMS. After 3 hrs LCMS shows no starting material and the major component at a retention time 13.4 min (82.8%) (m/e 651). The yellow solution is cooled in an ice bath, diluted with EtOAc (250 mL) and washed with ice cold 3 N sodium hydroxide until neutral/basic. The organic layer is washed with brine (100 mL) dried (MgSO$_4$) and evaporated to a light tan oil. Refluxing methanol (100 mL) is added, the mixture is stirred, seeded and cooled in an ice bath yielding light tan crystals. After cooling for 30 min, the crystals are collected by filtration and dried in the vacuum oven at ambient temperature over night (7.06 g, 74.3% from hydrazone 4). Compound 8A is optionally recrystallized from EtOAc/methanol (dissolving in 40 mL of refluxing EtOAc and adding 50 mL refluxing methanol to the stirring solution provides white crystals of 8A (5 g). LCMS retention time 13.4 min (91%) (m/e 651).

Example

Bazedoxifene acetate (9A). See, generally, Miller et al., in J. Med. Chem. 2001, 44, 1654-1657. 1-(4-(2-(Azepan-1-yl)ethoxy)benzyl)-5-(benzyloxy)-2-(4-benzyloxy)phenyl)-3-methyl-1H-indole (8A) (2.0 g, 3.07 mmol) is dissolved in tetrahydrofuran (100 mL) in a 500 mL round bottom flask with a stirring bar and sodium ascorbate (100 mg) is added followed by ethanol (100 mL). The flask is blanketed with argon, 10% Pd/C (200 mg) is added and the flask is covered with a rubber septum. The reaction mixture is blanketed with hydrogen (balloon) and stirred for 15 h at ambient temperature. TLC (CH$_2$Cl$_2$:MeOH 9:1) shows the disappearance of 8A, R$_f$~0.6 and a single new spot (Rf~0.1, LCMS retention time 8.6 min, m/e 471). The hydrogenation reaction is filtered through a Celite pad, washed with ethanol (25 mL) and the filtrate is evaporated to a colorless oil. The oil is dissolved in acetone (30 mL) and heated to 35° C. with stirring. Seed crystals of bazedoxifene acetate (9) are added to the solution and glacial acetic acid (200 mg, 3.3 mmol) in acetone (1 mL) is slowly added. The solution is allowed to cool to room temp slowly resulting in white crystals. Stirring is continued for 1 hr and the crystals are collected by filtration, washed with cold acetone (−15° C.) and dried in a vacuum at 40° C. for 1 hr, (1.4 g, 97%). LCMS retention time 7.95 min (100%) m/e 471; mp 168-169° C. (Lit mp 170.5-172.5° C.), NMR (DMSO-d6) δ 11.89 (br s, 1H), 9.67 (br s, 1H), 8.68 (br s, 1H), 7.15 (d, 2H, J=8.5 Hz). 7.06 (d, 1H, J=8.7 Hz), 6.85 (d, 2H, J=8.5 Hz), 6.80 (d, 1H, J=2.3 Hz), 6.75 (d, 2H, J=9.0 Hz), 6.74 (d, 2H, J=9.0 Hz), 6.57 (dd, 1H, J=8.7 Hz, 2.3 Hz), 5.10 (s, 2H), 3.93 (t, 2H, J=6.1 Hz), 2.77 (t, 2H, J=6.1 Hz), 2.63 (m, 4H), 2.10 (s, 3H), 1.91 (s, 3H), 1.47-1.58 (m, 8H).

What is claimed is:

1. A process for preparing a compound of the formula

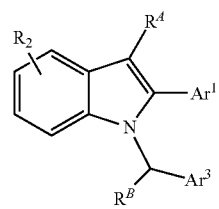

or a pharmaceutically acceptable salt thereof, comprising:

(d) contacting a compound of the formula

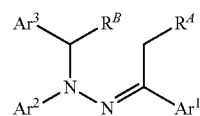

with an acid; or (c) contacting a first compound of the formula

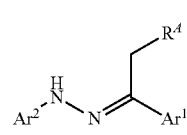

with a second compound of the formula

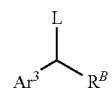

or a salt thereof, and a base; or (b) contacting a first compound of the formula

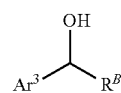

or a salt thereof, with a reagent capable of converting the hydroxyl group into a leaving group to form a second compound of the formula

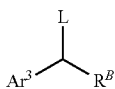

or a salt thereof, where L is the leaving group; or
(a) contacting a first compound of the formula

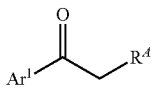

with a second compound of the formula

Ar²—NHNH₂ or a salt thereof; or
a combination of any of the foregoing steps; wherein
Ar¹ and Ar² are each aryl, each of which is independently optionally substituted;
Ar³ is a group of the formula

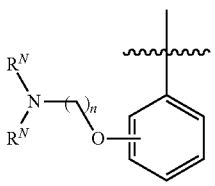

wherein n is 2, 3, 4, or 5; and each $R^N$ is independently selected from hydrogen, alkyl, heteroalkyl, arylalkyl, and heteroarylalkyl, each of which is optionally substituted, or both $R^N$ and the attached nitrogen are taken together to form a cycloheteroalkyl;
$R^A$ is hydrogen, or optionally substituted alkyl or optionally substituted arylalkyl;
$R^B$ is hydrogen, or optionally substituted alkyl or optionally substituted arylalkyl; and
$R^2$ is hydrogen, or represents one or more optional substituents.

2. The process of claim 1, wherein the second compound in step (a) is a salt; and step (a) is performed in the presence of less than about 1 equivalent of a base.

3. The process of claim 2, wherein the base is an inorganic base.

4. The process of claim 1, wherein the reagent in step (b) capable of converting the hydroxyl group into a leaving group is a halogenating agent.

5. The process of claim 1, wherein the base in step (c) is a hydride base.

6. The process of claim 1, wherein the acid in step (d) is a carboxylic acid.

7. The process claim 1, wherein Ar¹ and Ar² are each independently a protected phenol.

8. The process of claim 7, wherein Ar¹ and Ar² are 4-benzyloxyphenyl.

9. The process of claim 8 further comprising, contacting the compound of the formula

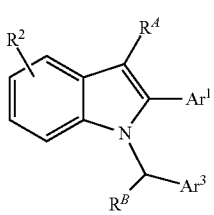

with a reducing agent.

10. The process of claim 9, wherein the reducing agent is hydrogen gas in the presence of a metal catalyst, and the metal catalyst is palladium on carbon, to provide a deprotected phenol compound of the formula

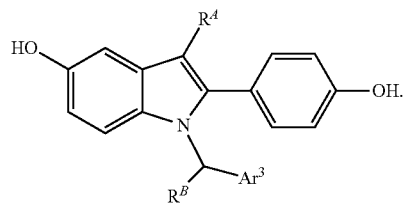

11. The process of claim 1, wherein the compound of the formula

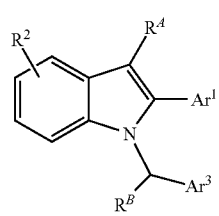

or a pharmaceutically acceptable salt thereof, has the formula

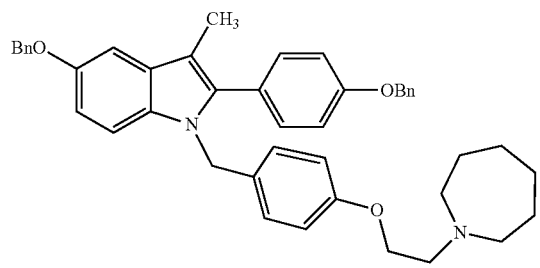 [SMILES: Cc1c(-c2ccc(OCc3ccccc3)cc2)n(Cc2ccc(OCCN3CCCCCC3)cc2)c2ccc(OCc3ccccc3)cc12]

or a pharmaceutically acceptable salt thereof.

12. The process of claim 10, further comprising crystallizing the deprotected phenol compound in the presence of an acid, or a carboxylic acid, or acetic acid to form an acid addition salt thereof.

13. The process of claim 1, wherein $R^A$ is methyl.

14. The process of claim 1, wherein $R^B$ is hydrogen.

15. The process of claim 1, wherein Ar³ is a radical of the formula

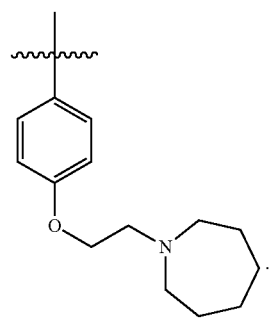

16. The process of claim 1, wherein the first compound of step (c) is of the formula

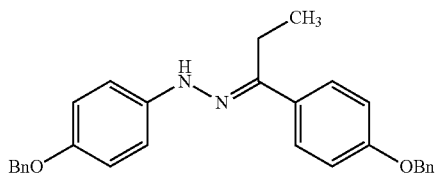 [SMILES: CC/C(=N\Nc1ccc(OCc2ccccc2)cc1)c1ccc(OCc2ccccc2)cc1]

or a salt thereof.

17. The process of claim 1, wherein the second compound of step (c) is of the formula

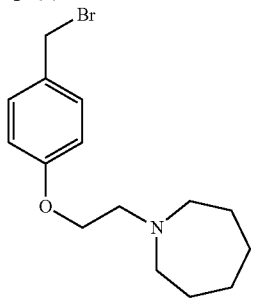

or a salt thereof.

18. The process of claim 1, wherein the compound of step (d) is of the formula

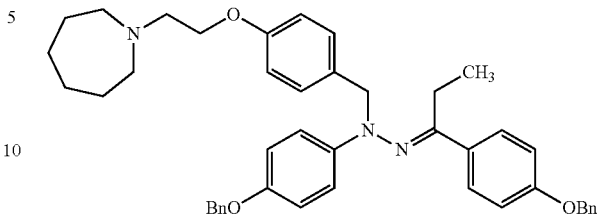

or a salt thereof.

19. The process of claim 3, wherein the inorganic base in step (a) is NaHCO₃.

20. The process of claim 4, wherein the halogenating agent of step (b) is PBr₃.

21. The process of claim 5, wherein the hydride base of step (c) is NaH.

22. The process of claim 6, wherein the carboxylic acid of step (d) is acetic acid.

* * * * *